(12) United States Patent
Lee et al.

(10) Patent No.: US 9,163,134 B2
(45) Date of Patent: Oct. 20, 2015

(54) HIGHLY FUNCTIONAL ADDITIVE FOR POLYMERIZATION AND METHOD FOR PREPARING VINYL CHLORIDE SEEDS USING THE SAME

(71) Applicant: LG CHEM, LTD., Seoul (KR)

(72) Inventors: Hyun Sup Lee, Daejeon (KR); Kyung Seog Youk, Daejeon (KR); Han Hong Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/178,044

(22) Filed: Feb. 11, 2014

(65) Prior Publication Data

US 2014/0200309 A1    Jul. 17, 2014

Related U.S. Application Data

(63) Continuation of application No. PCT/KR2012/006220, filed on Aug. 6, 2012.

(30) Foreign Application Priority Data

| Sep. 2, 2011 | (KR) | 10-2011-0088862 |
|---|---|---|
| Feb. 3, 2012 | (KR) | 10-2012-0011522 |
| Feb. 6, 2012 | (KR) | 10-2012-0011621 |
| May 15, 2012 | (KR) | 10-2012-0051703 |
| May 15, 2012 | (KR) | 10-2012-0051705 |

(51) Int. Cl.
| C08K 5/42 | (2006.01) |
|---|---|
| C07C 31/125 | (2006.01) |
| C07C 31/02 | (2006.01) |
| C08F 114/06 | (2006.01) |
| C08F 6/00 | (2006.01) |
| B01J 19/18 | (2006.01) |
| C08F 14/06 | (2006.01) |
| C08K 5/05 | (2006.01) |
| C08F 2/26 | (2006.01) |

(52) U.S. Cl.
CPC . *C08K 5/42* (2013.01); *B01J 19/18* (2013.01); *C07C 31/02* (2013.01); *C07C 31/125* (2013.01); *C08F 2/26* (2013.01); *C08F 6/003* (2013.01); *C08F 6/006* (2013.01); *C08F 14/06* (2013.01); *C08F 114/06* (2013.01); *C08K 5/05* (2013.01); *C08F 2500/24* (2013.01)

(58) Field of Classification Search
USPC .......................................... 524/745; 568/840
See application file for complete search history.

(56) References Cited

U.S. PATENT DOCUMENTS 6,949,601 B1    9/2005   Leth-Olsen et al.
2009/0311531 A1*  12/2009  Youk et al. .................... 428/402

FOREIGN PATENT DOCUMENTS

| CN | 101613429 A | 12/2009 |
|---|---|---|
| JP | 05-239145 | 9/1993 |
| JP | 08-067705 | 3/1996 |
| JP | 1996-067705 A | 3/1996 |
| KR | 10-2010-0042159 | 4/2010 |

OTHER PUBLICATIONS

"Carboxyl Carrying-Large Uniform Latex Particles"; Tuncel, et al.; Colloids and Surfaces; A Physiochemical and Engineering Aspects; vol. 197; Issue 1-3, pp. 79-94; Feb. 28, 2002.

* cited by examiner

*Primary Examiner* — Robert Harlan
(74) *Attorney, Agent, or Firm* — Dentons US LLP

(57) ABSTRACT

Disclosed is a method for preparing a vinyl chloride seed, comprising adding a vinyl chloride monomer, an emulsifier and a polymerization initiator to an aqueous medium, homogenizing droplets using a homogenizer pump, and polymerizing the homogenized droplets. The method provides a more stable latex by minimizing residual monomers by performing polymerization after adding a higher aliphatic alcohol serving as a monomer absorption enhancer and then performing homogenization, and additionally, improves productivity and reduces amount of scale generated by increasing the efficiency of monomer consumption during polymerization. Further, by applying the vinyl chloride-based seed to seed emulsion polymerization of vinyl chloride resins, polymer reactivity is improved, the reaction time of the seed emulsion polymerization is effectively reduced, the sizes of small and large particles are controlled and the particle diameter of the vinyl chloride resin is thus controlled.

24 Claims, 2 Drawing Sheets

HIGHLY FUNCTIONAL ADDITIVE FOR POLYMERIZATION AND METHOD FOR PREPARING VINYL CHLORIDE SEEDS USING THE SAME

This application is a Continuation Bypass of International Application PCT/KR2012/006220, with an international filing date of Aug. 6, 2012, which claims priority to and the benefit of Korean Patent Application No. 10-2011-0088862, filed on Sep. 2, 2011, Korean Patent Application No. 10-2012-0011522, filed on Feb. 3, 2012, Korean Patent Application No. 10-2012-0011621, filed on Feb. 6, 2012, Korean Patent Application No. 10-2012-0051703, filed on May 15, 2012, and Korean Patent Application No. 10-2012-0051705, filed on May 15, 2012, all of which are incorporated herein by reference in their entirety.

TECHNICAL FIELD

The present invention relates to a monomer absorption accelerator for preparing vinyl chloride resins and a method for preparing vinyl chloride seeds using the same. More specifically, the present invention relates to a monomer absorption accelerator for preparing vinyl chloride resins and a method for preparing vinyl chloride seeds using the same, wherein higher aliphatic alcohol serving as a monomer absorption accelerator for preparing vinyl chloride resins is added before polymerization to minimize an amount of residual monomers and thus obtain a more stable latex and to increase consumption efficiency of monomers and polymerization reactivity during polymerization.

BACKGROUND ART

A paste vinyl chloride resin, which is a general-purpose resin globally the most widely used in household and industrial applications, is prepared by a common method such as emulsion polymerization, micro-suspension polymerization or seed emulsion polymerization.

In accordance with seed emulsion polymerization, the paste vinyl chloride resin is prepared by adding two types of seeds having different mean particle sizes in an early stage of polymerization and growing a vinyl chloride monomer while reacting the vinyl chloride monomer with the seeds to prepare final latex particles.

Of these two types of seeds, the first seed is prepared by adding a vinyl chloride monomer, an emulsifier and a fat-soluble polymerization initiator, homogenizing the components using a rotor-stator type homogenizer pump and polymerizing the resulting substance. The second seed is prepared by emulsion polymerization. The first seed comprises the fat-soluble polymerization initiator in particles thereof and thus inherently has reaction sites. Accordingly, it is necessary that a suitable amount of initiator be left in particles after completion of polymerization through addition of excess initiator during polymerization of the first seed so as to facilitate polymerization initiation during seed emulsion polymerization.

In general, polymerization temperature is adjusted to a low level of 50° C. or less and an initiator having long half-life such as lauryl peroxide (LPO) is used so as to allow a predetermined amount of initiator to remain un-decomposed in particles of the first seed. The particle size of the first seed, and the type or content of remaining initiator are factors greatly affecting polymerization reactivity. Accordingly, there is a need for methods effectively controlling these factors to improve polymerization reactivity.

A variety of additives, in addition to the monomer and the emulsifier, are used for polymerization to prepare vinyl chloride resins according to desired application and physical properties. An ionic or non-ionic emulsifier may be added to improve latex stability, or an acid or base may be used to control hydrogen ion level. Among the ionic and non-ionic emulsifiers, substances used as the non-ionic emulsifier are considerably varied and results change according to the type of non-ionic emulsifier. Accordingly, selection of a substance suitable for the desired application is considerably essential and the desired properties can be easily and simply obtained.

DISCLOSURE

Technical Problem

Therefore, it is one object of the present invention to provide a monomer absorption accelerator for preparing vinyl chloride resins which minimizes an amount of remaining monomer which affects physical properties of final latex after polymerization of vinyl chloride resins to obtain a more stable latex and additionally increases monomer consumption efficiency during polymerization, improves production efficiency and reduces an amount of scale generated.

It is another object of the present invention to provide vinyl chloride seeds for paste vinyl chloride resins which exhibit superior polymerization reactivity when used for seed emulsion polymerization by adding a certain type of monomer absorption accelerator before homogenization of the vinyl chloride seeds.

Technical Solution

When the seeds prepared according to the present invention, the monomer absorption accelerator contained in the seeds stabilizes droplets during emulsion polymerization and increases the rate and concentration of vinyl chloride monomer incorporated into the seeds when applied to main polymerization and thereby improves reactivity, thus enabling preparation of paste vinyl chloride resins having a large average particle diameter without increasing generation of scale. In addition, properties, such as viscosity, of plastisol can be improved based on such a resin.

The object and other objects can be accomplished by the present invention described below.

In accordance with one aspect of the present invention, the above and other objects can be accomplished by the provision of a monomer absorption accelerator for preparing vinyl chloride resins, represented by the following Formula 1.

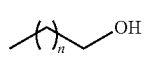

[Formula 1]

wherein n is an integer of 4 to 24.

In accordance with another aspect of the present invention, provided is a method for preparing vinyl chloride seeds including adding a vinyl chloride monomer, an emulsifier and a polymerization initiator to an aqueous medium, homogenizing droplets using a homogenizer pump and performing polymerization, wherein the monomer absorption accelerator represented by the following Formula 1 is added before the polymerization and polymerization is performed after the homogenization.

In accordance with another aspect of the present invention, provided are vinyl chloride seeds obtained by the method for preparing vinyl chloride seeds, wherein the particle diameter (MV) of the vinyl chloride seeds obtained is varied under the same homogenization conditions according to the type and amount of the higher aliphatic alcohol used.

BEST MODE

Figure 1:
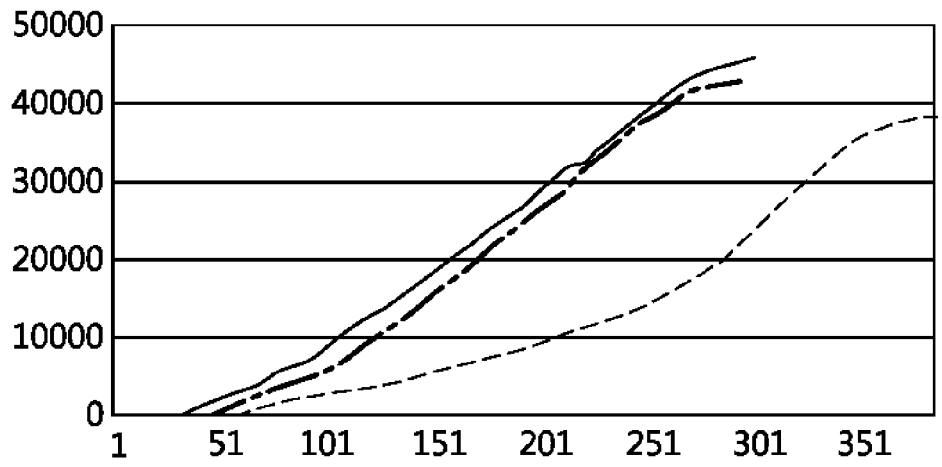
FIG. 1 is a graph showing total cumulative amounts of removed heat as a function of polymerization time in cases in which a monomer absorption accelerator is used and in cases in which a monomer absorption accelerator is not used according to Examples and Comparative Example of the present invention.
Figure 2:
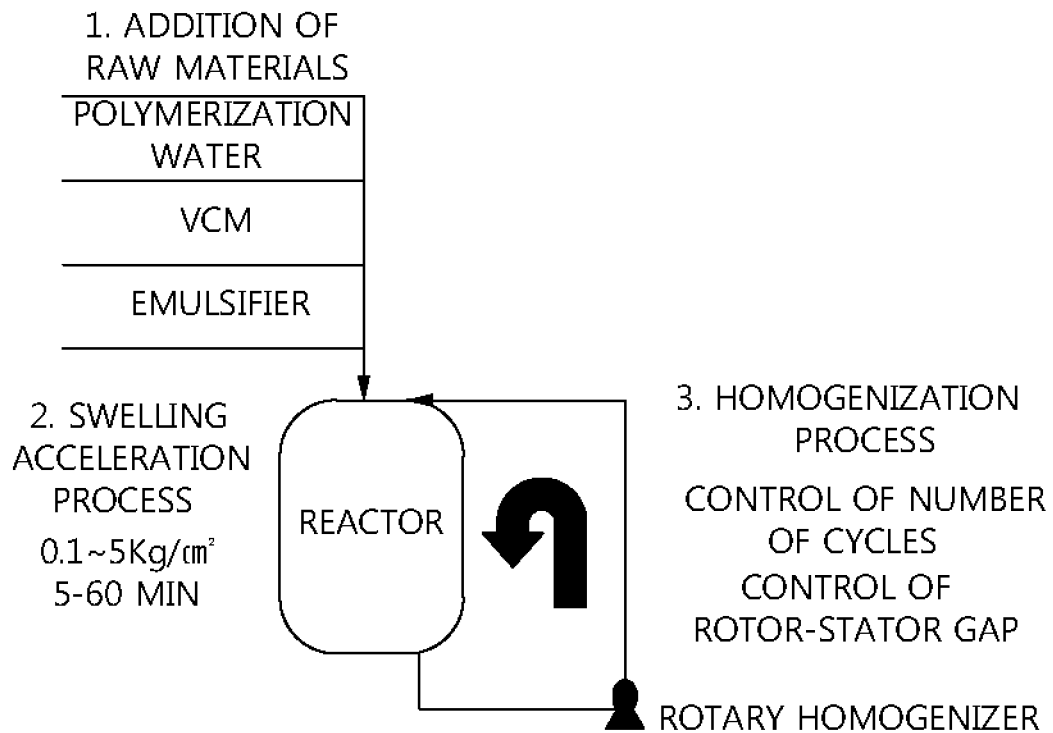
FIG. 2 is a schematic diagram illustrating a method for preparing a vinyl chloride seed in accordance with an embodiment of the present invention.
Figure 3:
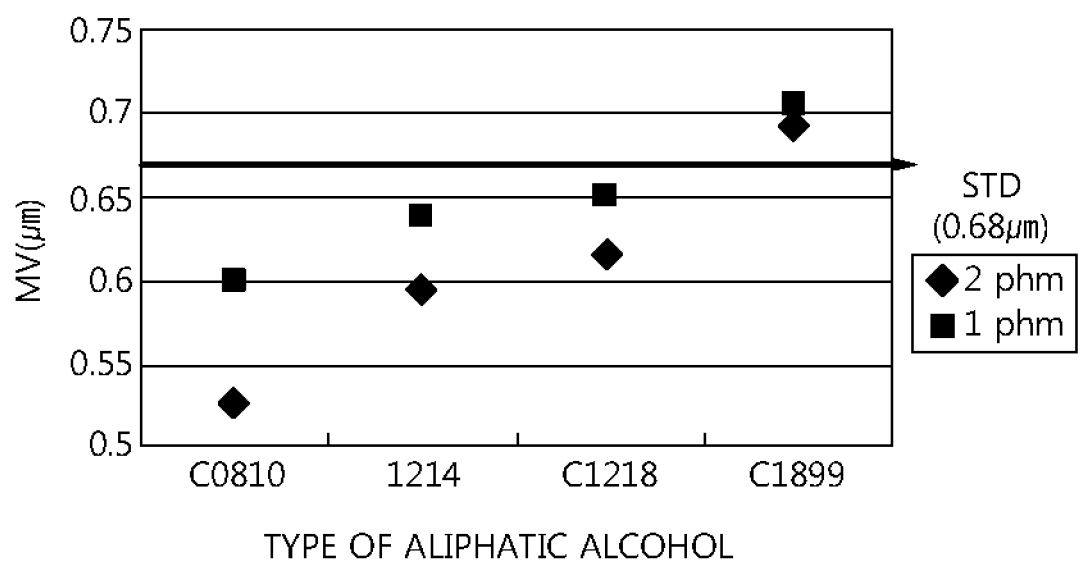
FIG. 3 is a graph showing variation in average particle diameter according to the type of monomer absorption accelerator. STD represents particle diameter in a case in which the monomer absorption accelerator is not used.

In accordance with the present invention, provided is a monomer absorption accelerator for preparing vinyl chloride resins, represented by the following Formula 1.

[Formula 1]

wherein n is an integer of 4 to 24.

The present invention minimizes an amount of remaining monomer by adding higher aliphatic alcohol serving as the monomer absorption accelerator before polymerization.

The higher aliphatic alcohol used for polymerization has the following structure. The higher aliphatic alcohol is added during polymerization of the vinyl chloride resin.

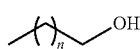

[Formula 1]

wherein n is an integer of 4 to 24 and the higher aliphatic alcohol may be unsaturated or saturated.

Specifically, n is an integer of 4 to 24, and more specifically, n is an integer of 8 to 18. Within this range, permeation into latex particles is facilitated.

The higher aliphatic alcohol is a $C_8$-$C_{18}$ higher aliphatic alcohol and is specifically selected from the group consisting of $C_8$ higher aliphatic alcohol, $C_{10}$ higher aliphatic alcohol, $C_{12}$ higher aliphatic alcohol, $C_{14}$ higher aliphatic alcohol, $C_{16}$ higher aliphatic alcohol, $C_{18}$ higher aliphatic alcohol and a mixture thereof.

That is, the higher aliphatic alcohol may be a mixture of $C_8$ higher aliphatic alcohol and $C_{10}$ higher aliphatic alcohol in a weight ratio of $C_8$:$C_{10}$=0~100:0~100, more specifically in a weight ratio of $C_8$:$C_{10}$=0~55:0~45. In addition, a $C_{12}$-$C_{18}$ aliphatic alcohol compound may be used alone or as a mixture thereof. A content of each aliphatic alcohol compound may be 0 to 100% by weight, in particular, a content of $C_{12}$ or $C_{14}$ aliphatic alcohol is 60% by weight or more. The present invention controls solubility in water by variously selecting an alkyl chain length of monomer absorption accelerator. A vinyl chloride monomer (VCM) used for PVC polymerization does not readily permeate into the surface or the inside of PVC particles covered with a general emulsifier, because it is a fat-soluble substance which is insoluble in water. Accordingly, when the monomer absorption accelerator is used, the fat-soluble accelerator present between emulsifier particles facilitates access of the monomer to the surface of PVC particles. The position of the monomer present in particles is changed according to the chain length of the monomer absorption accelerator used. Accordingly, solubility of the fat-soluble accelerator is controlled and the monomer is disposed on the surface of emulsifier particles through control of the chain length of the monomer absorption accelerator.

In accordance with the present invention, respective vinyl chloride resin seeds are polymerized by separately adding monomer absorption accelerators having different chain lengths. Reaction time reduction caused by decrease in particle size is prevented by uniformizing the particle size through control of the number of cycles of the homogenizer. After addition of seeds thus polymerized, seed emulsion polymerization is performed and polymerization time reduction according to chain length is compared.

That is, the present invention provides a monomer absorption accelerator for preparing vinyl chloride resins characterized in that the monomer absorption accelerator is higher aliphatic alcohol having a solubility in water, of 10,000 to 0.001 mg/L. For example, the monomer absorption accelerator for preparing vinyl chloride resins has a solubility in water, of 800 to 0.1 mg/L. The higher aliphatic alcohol having the solubility within the range defined above has the effects of reducing polymerization reaction time during main polymerization, improving production efficiency and enhancing latex stability.

Higher aliphatic alcohol having 8 to 14 carbon atoms is preferably used in consideration of the fact that reaction time is more effectively reduced as chain length of higher aliphatic alcohol decreases.

In addition, the monomer absorption accelerator for preparing vinyl chloride resins is used in an amount of 0.1 to 10 phm (with respect to the weight of the vinyl chloride monomer) for preparation of vinyl chloride polymers, thus minimizing an amount of remaining monomer which affects physical properties of a final latex after completion of polymerization of vinyl chloride resins and obtaining more stable latex. More specifically, the monomer absorption accelerator is used in an amount of 0.5 to 3 phm. When the amount of the monomer absorption accelerator is below the lower limit, particle control of the final paste vinyl chloride resin is insufficient and when the amount thereof is higher than the upper limit, the monomer absorption accelerator occupies the original position of the emulsifier, thus disadvantageously causing deterioration in stability.

TABLE 1

Solubility of alcohol in water

| Alcohol | Solubility in water (mg/L) | |
| --- | --- | --- |
| $CH_3$—OH | ∞ | Water soluble |
| $C_2H_5$—OH | ∞ | |
| $C_3H_7$—OH | ∞ | |
| $C_4H_9$—OH | 63200 | |
| $C_5H_{11}$—OH | 22000 | |
| $C_6H_{13}$—OH | 6260 | |
| $C_7H_{15}$—OH | 1800 | |
| $C_8H_{17}$—OH | 540 | |
| $C_9H_{19}$—OH | 140 | Oil soluble |
| $C_{10}H_{21}$—OH | 37 | |
| $C_{12}H_{25}$—OH | 4 | |

TABLE 1-continued

| Solubility of alcohol in water | |
|---|---|
| Alcohol | Solubility in water (mg/L) |
| $C_{14}H_{29}$—OH | 0.191 |
| $C_{16}H_{33}$—OH | 0.0412 |
| $C_{18}H_{37}$—OH | 0.0011 |

Specifically, examples of the higher alcohol include $C_8$-$C_{10}$ alcohol (produced by LG household & healthcare Co. Ltd. under the trade name of ELOCOL C0810 as described in Example below), $C_{12}$-$C_{14}$ alcohol (produced by LG household & healthcare Co. Ltd. under the trade name of ELOCOL C1214 as described in Example below), $C_{12}$-$C_{18}$ alcohol (stripped palm kernel lauryl alcohol, produced by LG household & healthcare Co. Ltd. under the trade name of ELOCOL C1218) or stearyl alcohol ($C_{18}$ 99%, solid, produced by LG household & healthcare Co. Ltd. under the trade name of ELOCOL C1899) and the like. The chloride paraffin is for example Plastoil 152 (trade name) produced by Handy Chemical Corporation, etc. as described in Example below.

The present invention provides a method for preparing vinyl chloride seeds including adding a vinyl chloride monomer, an emulsifier and a polymerization initiator to an aqueous medium, homogenizing droplets using a homogenizer pump and performing polymerization, wherein a monomer absorption accelerator represented by the following Formula 1 is added before the polymerization and polymerization is performed after the homogenization.

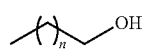

[Formula 1]

wherein n is an integer of 4 to 24 and the structure of Formula 1 may be unsaturated or saturated.

The method for preparing vinyl chloride seeds specifically comprises swelling acceleration including adding polymerization water, a vinyl chloride monomer, an emulsifier and the monomer absorption accelerator to a pre-mixing tank, followed by agitating to obtain a mixture, passing the mixture through a rotary homogenizer to homogenize the mixture and polymerizing the homogenized mixture in a reactor.

The method enables production of particles while controlling the number of cycles of the rotary homogenizer. Primarily, the monomer absorption accelerator, a minor ingredient and a monomer are added to a pre-mixing tank, followed by agitating under vacuum. Then, the mixture is passed through the rotary homogenizer to produce droplets and the droplets are polymerized to obtain seeds with a desired particle size. The particles with the desired size are prepared by controlling the number of cycles and rotor-stator gap during homogenization. Before passing the mixture through the homogenizer, the fat-soluble monomer absorption accelerator is sufficiently agitated at a pressure of about 0.1 to 5 kg/cm² for about 5 to about 60 minutes. This process is referred to as a "swelling acceleration process". The latex produced through this process exhibits high droplet stability and enables production of particles having a size which is difficult to stably obtain using a conventional emulsifier control manner. In addition, when seed emulsion polymerization is performed using the seeds thus prepared, the effect of reducing polymerization time to about 30 minutes or longer can be obtained.

20 to 150 parts by weight of the polymerization water, 0.1 to 10 parts by weight of the emulsifier and 0.1 to 10 parts by weight of the monomer absorption accelerator are added, based on 100 parts by weight of the vinyl chloride monomer.

The swelling acceleration step is carried out by agitating at a pressure of 0.1 to 5 kg/cm² for 5 to 60 minutes.

In addition, the homogenization step is carried out using a homogenization pump for 1 to 3 hours. The number of cycles of the rotary homogenizer is 10 to 150, specifically, 20 to 85. In addition, the rotor-stator gap may be 0.05 to 10 mm, specifically 0.1 to 1 mm. When the number of cycles is excessively small, particle size slightly increases and particle distribution broadens, and when the number of cycles is excessively great, it takes a long time and particle distribution is excessively narrow. As the gap becomes narrow, the particle size is decreased and as the gap is excessively great, it is difficult to obtain uniform particles and stability is low.

The emulsifier comprises at least one selected from the group consisting of sodium lauryl sulfate (SLS), sodium dodecyl benzene sulfonate (SDBS), sodium dodecyl alkylsulfate (SDS), ammonium lauryl sulfate (ALS), sodium cetyl stearyl sulfate, sodium lauryl ether sulfate (SLES) and succinate. Specifically, sodium dodecyl benzene sulfonate is used, but the present invention is not limited thereto.

The emulsifier may be an anionic emulsifier, a nonionic emulsifier or a combination thereof.

Examples of the anionic emulsifier include carboxylic acid, alkyl sulfonic acid, alkyl benzene sulfonic acid, succinic acid sulfonate, α-olefin sulfonate, alkyl phosphate and the like. The anionic emulsifier may be used in an amount of 1 part by weight or less, with respect to 100 parts by weight of the vinyl chloride monomer. When the anionic emulsifier is used in the content defined above, mechanical stability of polymer and latex is advantageously superior.

Examples of the nonionic emulsifier include polyoxyethylene ether, polyoxyethylene alkyl phenyl ether, polyoxyethylene alkenyl ether, polyoxyethylene derivatives, glycerin fatty acid ester, sorbitan fatty acid ester, polyoxyethylene fatty acid ester, silicone emulsifiers, polyethylene glycol and derivatives thereof, and polypropylene-glycol and derivatives thereof and the like. The content of nonionic emulsifier is not limited and may be 3 parts by weight or less, with respect to 100 parts by weight of the vinyl chloride monomer.

The emulsifier may be added batchwise to the aqueous medium before seed emulsion polymerization or may be continuously added thereto during seed emulsion polymerization, or may be added to the latex after completion of polymerization. If necessary, the emulsifier may be added in a combination of these addition methods.

The first seed may be prepared by micro-suspension polymerization. That is, the first seed is obtained by adding the vinyl chloride monomer, the emulsifier, the polymerization initiator and the swelling accelerator to the aqueous medium, homogenizing droplets using a homogenizer pump and polymerizing the resulting droplets.

The polymerization initiator is a fat-soluble polymerization initiator and examples thereof include organic peroxide polymerization initiators such as peroxy dicarbonates, for example, propyl peroxy dicarbonate, and peroxy esters, for example t-butylperoxypivalate and t-butylperoxyneodecanoate and azo polymerization initiators such as 2,2-azobisisobutyronitrile. This compound may be used as the polymerization initiator alone or in combination thereof. The polymerization initiator may be preferably used in an amount of 0.01 to 10 phm, based on 100 phm of the vinyl chloride monomer.

The vinyl chloride seeds may be prepared by adding components to the aqueous medium, homogenizing droplets using a rotor stator-type homogenizer pump and polymerizing the resulting droplets.

The homogenization may be carried out for 1 to 3 hours, but the present invention is not limited thereto. The homogenizer pump may be of a rotor-stator type.

In addition, the polymerization may be carried out at a temperature of 40 to 50° C. for 9 to 12 hours.

In accordance with an embodiment of the present invention, provided is a monomer absorption accelerator-based composition for vinyl chloride resins, comprising a vinyl chloride monomer, an emulsifier, an initiator and a polymerization inhibitor, wherein the composition comprises the higher aliphatic alcohol of Formula 1.

The higher aliphatic alcohol serves as both a monomer absorption accelerator and an auxiliary emulsifier.

In addition, in accordance with another embodiment of the present invention, provided is a method for polymerizing a latex using the monomer absorption accelerator-based vinyl chloride resin composition, the method comprising adding reaction water, an initiator, a polymerization inhibitor, a monomer absorption accelerator, a vinyl chloride monomer and an emulsifier to a reactor for latex polymerization, followed by homogenization and polymerization.

The type and amount of the monomer absorption accelerator added may be determined according to particle diameter of paste vinyl chloride resin to be finally obtained.

In accordance with another embodiment of the present invention, provided is a paste vinyl chloride resin obtained by the latex polymerization method, wherein a particle diameter (MV) of the paste vinyl chloride resin is varied under the same homogenization conditions according to the type and amount of the higher aliphatic alcohol used.

In addition, in accordance with another embodiment of the present invention, provided is a vinyl chloride seed prepared by the method for preparing the vinyl chloride seed. In accordance with another embodiment of the present invention, provided is a paste vinyl chloride resin prepared by performing seed emulsion polymerization using 3 to 15 phm of the vinyl chloride seed as a first seed at 50 to 65° C.

A vinyl chloride seed having an average particle diameter of 0.3 to 1.5 μm can be obtained by the method. When such a seed is applied to seed emulsion polymerization of paste vinyl chloride resins, polymerization time is reduced, generation of scale is not increased and a paste vinyl chloride resin having an increased average particle diameter can be prepared. In addition, such a resin contributes to improvement of viscosity of plastisol.

The seed emulsion polymerization of the paste vinyl chloride resin is carried out by adding a vinyl chloride monomer, an emulsifier, a first seed, a second seed, a buffer and a redox catalyst to an aqueous medium, followed by polymerization.

80 to 98 wt % of the vinyl chloride monomer used for paste vinyl chloride resin polymerization is generally converted into the paste vinyl chloride resin and the non-reacted monomer is removed. The latex of the paste vinyl chloride resin after polymerization is obtained by spray drying. During drying, a process such as dehydration and filtration is generally not performed. For this reason, the raw material such as emulsifier remains in the resin. The paste vinyl chloride resin preferably has a particle diameter of 0.1 to 50 μm in terms of good dispersibility of plasticizer and suitability for paste processing.

In addition, when the seeds are applied to seed emulsion polymerization, a paste vinyl chloride resin can be obtained, which does not increase generation of scale, exhibits polymerization stability and has an average particle diameter of 0.1 to 15 μm. Specifically, as can be seen from Example described below, the paste vinyl chloride resin can be prepared by performing seed emulsion polymerization using 3 to 5 phm of the vinyl chloride seed prepared according to the present invention as the first seed at 50 to 65° C., although the present invention is not limited thereto.

Paste vinyl chloride resin particles having different sizes can be obtained when prepared under the same cycle condition by controlling the type and amount of the higher aliphatic alcohol according to particle diameter of final paste vinyl chloride resin.

Vinyl chloride seeds having an average particle diameter of 0.4 to 1.5 μm can be prepared by the method according to the present invention. When C810 was used, the average particle diameter was increased by about 25% to about 6%, when C1214 was used, the average particle diameter was decreased by about 14% to about 7%, and when C1218 was used, the average particle diameter was decreased by about 11% to about 9%, and when C1899 was used, the average particle diameter was increased by about 0.5% to about 2.5%.

Hereinafter, the present invention will be described in detail.

Hereinafter, preferred examples will be provided for better understanding of the present invention. These examples are only provided to illustrate the present invention and it will be apparent to those skilled in the art that various modifications and alterations are possible within the scope and technical range of the present invention. Such modifications and alterations fall within the scope of claims included herein.

EXAMPLE

[Testing Associated with First Seed Polymerization]

Example 1

111 phm of deionized water, 1.8 phm of lauryl peroxide, 0.001 phm of paraquinone and 2 phm of higher alcohol (produced by LG household & healthcare Co. Ltd. under the trade name of ELOCOL C0810) as a monomer absorption accelerator were added to a 200 L high-pressure reactor while agitating using an agitator at 40 rpm and −730 mmHg of vacuum was applied to the reactor. 100 phm of a vinyl chloride monomer and 1.5 phm of 15% sodium dodecyl benzene sulfonate were added to the vacuum-reactor, followed by agitating for 15 minutes.

The inner temperature of the reactor was decreased to 20° C. or less and homogenization was performed using a rotor stator-type homogenizer for 2 hours. After completion of homogenization, the temperature of the reactor was adjusted to 43° C. and polymerization was performed.

After 652 minutes during which the pressure of the reactor reached 3.5 kg/cm², the reaction was completed and the unreacted vinyl chloride monomer was recovered and removed to obtain a first seed latex having an average particle diameter of 0.52 μm.

Example 2

The same testing as in Example 1 was repeated except that 1 phm of ELOCOL C0810 was added instead of 2 phm of ELOCOL C0810, the reaction was completed after 595 minutes during which the pressure of the reactor reached 3.5 kg/cm², and the unreacted vinyl chloride monomer was recovered and removed to obtain a first seed latex having an average particle diameter of 0.62 μm.

Example 3

The same testing as in Example 1 was repeated except that 2 phm of ELOCOL C1214 (produced by LG household & healthcare Co. Ltd. under the trade name of ELOCOL C1214) was added, instead of 2 phm of ELOCOL C0810, the reaction was completed after 568 minutes during which the pressure of the reactor reached 3.5 kg/cm$^2$, and the unreacted vinyl chloride monomer was recovered and removed to obtain a first seed latex having an average particle diameter of 0.59 μm.

Example 4

The same testing as in Example 3 was repeated except that 1 phm of ELOCOL C1214 was added, instead of 2 phm of ELOCOL C1214, the reaction was completed after 597 minutes during which the pressure of the reactor reached 3.5 kg/cm$^2$, and the unreacted vinyl chloride monomer was recovered and removed to obtain a first seed latex having an average particle diameter of 0.63 μm.

Example 5

The same testing as in Example 1 was repeated except that 2 phm of ELOCOL C1218 (produced by LG household & healthcare Co. Ltd. under the trade name of ELOCOL C1218) was added, instead of 2 phm of ELOCOL C0810, the reaction was completed after 612 minutes during which the pressure of the reactor reached 3.5 kg/cm$^2$, and the unreacted vinyl chloride monomer was recovered and removed to obtain a first seed latex having an average particle diameter of 0.63 μm.

Example 6

The same testing as in Example 5 was repeated except that 1 phm of ELOCOL C1218 was added, instead of 2 phm of ELOCOL C1218, the reaction was completed after 526 minutes during which the pressure of the reactor reached 3.5 kg/cm$^2$, and the unreacted vinyl chloride monomer was recovered and removed to obtain a first seed latex having an average particle diameter of 0.62 μm.

Example 7

The same testing as in Example 1 was repeated except that 2 phm of ELOCOL C1899 (produced by LG household & healthcare Co. Ltd. under the trade name of ELOCOL C1899) was added, instead of 2 phm of ELOCOL C0810, the reaction was completed after 579 minutes during which the pressure of the reactor reached 3.5 kg/cm$^2$, and the unreacted vinyl chloride monomer was recovered and removed to obtain a first seed latex having an average particle diameter of 0.69 μm.

Example 8

The same testing as in Example 7 was repeated except that 1 phm of ELOCOL C1899 was added, instead of 2 phm of ELOCOL C1899, the reaction was completed after 576 minutes during which the pressure of the reactor reached 3.5 kg/cm$^2$, and the unreacted vinyl chloride monomer was recovered and removed to obtain a first seed latex having an average particle diameter of 0.70 μm.

Example 9

The same testing as in Example 1 was repeated except that 2 phm of chloride paraffin (produced by Handy Chemical Corporation under the trade name of Plastoil 152) was added, instead of 2 phm of ELOCOL C0810, the reaction was completed after 592 minutes during which the pressure of the reactor reached 3.5 kg/cm$^2$, and the unreacted vinyl chloride monomer was recovered and removed to obtain a first seed latex having an average particle diameter of 0.74 μm.

Example 10

The same testing as in Example 9 was repeated except that 1 phm of chloride paraffin was added, instead of 2 phm of chloride paraffin, the reaction was completed after 574 minutes during which the pressure of the reactor reached 3.5 kg/cm$^2$, and the unreacted vinyl chloride monomer was recovered and removed to obtain a first seed latex having an average particle diameter of 0.71 μm.

Comparative Example 1

The same testing as in Example 1 was repeated except that 2 phm of ELOCOL C0810 was not added, the reaction was completed after 558 minutes during which the pressure of the reactor reached 3.5 kg/cm$^2$, and the unreacted vinyl chloride monomer was recovered and removed to obtain a first seed latex having an average particle diameter of 0.68 μm.

Comparative Example 2

The same testing as in Comparative Example 1 was repeated except that homogenization was performed using a rotor stator-type homogenizer for 3 hours, the reaction was completed after 541 minutes during which the pressure of the reactor reached 3.5 kg/cm$^2$, and the unreacted vinyl chloride monomer was recovered and removed to obtain a first seed latex having an average particle diameter of 0.62 μm.

[Testing Associated with Seed Emulsion Polymerization (Paste vinyl chloride Resin)]

Example 11

75 phm (part per hundred monomer) of deionized water and 4.6 phm of the first seed obtained in Example 2 were added to a 500 L high-pressure reactor and vacuum was then applied to the reactor while agitating.

100 phm of a vinyl chloride monomer was added to the vacuum-state reactor, the temperature of the reactor was elevated to 55° C. and seed emulsion polymerization was performed. After the polymerization was initiated, 0.8 phm of sodium lauryl sulfate was continuously added as an emulsifier to prepare a vinyl chloride latex.

When the pressure of the reactor reached 3.5 kg/cm$^2$ after 260 minutes, reaction was finished and the unreacted vinyl chloride monomer was recovered and removed to obtain a seed emulsion polymerization latex having a scale of 820 g. Then, the latex was spray-dried to prepare a powdery paste vinyl chloride resin.

Example 12

The same testing as in Example 11 was repeated except that the first seed of Example 4 was added, instead of the first seed of Example 2, the reaction was completed after 300 minutes during which the pressure of the reactor reached 3.5 kg/cm$^2$, and the unreacted vinyl chloride monomer was recovered and removed to obtain to obtain a seed emulsion polymerization latex having a scale of 800 g.

Example 13

The same testing as in Example 11 was repeated except that the first seed of Example 5 was added, instead of the first seed of Example 2, the reaction was completed after 294 minutes during which the pressure of the reactor reached 3.5 kg/cm², and the unreacted vinyl chloride monomer was recovered and removed to obtain to obtain a seed emulsion polymerization latex having a scale of 940 g.

Example 14

The same testing as in Example 11 was repeated except that the first seed of Example 6 was added, instead of the first seed of Example 2, the reaction was completed after 275 minutes during which the pressure of the reactor reached 3.5 kg/cm², and the unreacted vinyl chloride monomer was recovered and removed to obtain to obtain a seed emulsion polymerization latex having a scale of 780 g.

Example 15

The same testing as in Example 11 was repeated except that the first seed of Example 8 was added, instead of the first seed of Example 2, the reaction was completed after 326 minutes during which the pressure of the reactor reached 3.5 kg/cm², and the unreacted vinyl chloride monomer was recovered and removed to obtain to obtain a seed emulsion polymerization latex having a scale of 900 g.

Example 16

The same testing as in Example 11 was repeated except that the first seed of Example 10 was added, instead of the first seed of Example 2, the reaction was completed after 340 minutes during which the pressure of the reactor reached 3.5 kg/cm², and the unreacted vinyl chloride monomer was recovered and removed to obtain to obtain a seed emulsion polymerization latex having a scale of 240 g.

Comparative Example 3

The same testing as in Example 11 was repeated except that the first seed of Comparative Example 1 was added, instead of the first seed of Example 2, the reaction was completed after 375 minutes during which the pressure of the reactor reached 3.5 kg/cm², and the unreacted vinyl chloride monomer was recovered and removed to obtain to obtain a seed emulsion polymerization latex having a scale of 630 g.

Comparative Example 4

The same testing as in Example 11 was repeated except that the first seed of Comparative Example 2 was added, instead of the first seed of Example 2, the reaction was completed after 326 minutes during which the pressure of the reactor reached 3.5 kg/cm², and the unreacted vinyl chloride monomer was recovered and removed to obtain to obtain a seed emulsion polymerization latex having a scale of 670 g.

The average particle diameter and polymerization time in respective test examples were measured.

Average particle diameter: measured using NPA150 produced by Microtrac Inc.

Polymerization time: time until the pressure of the reactor reached 3.5 kg/cm² after elevation of the polymerization reactor temperature of the reactor was measured.

The measured values were summarized in the following Table 2 (first seed polymerization results) and Table 3 (seed emulsion polymerization results).

TABLE 2

| Item | Ex. 1 | Ex. 2 | Ex. 3 | Ex. 4 | Ex. 5 | Ex. 6 | Ex. 7 | Ex. 8 | Ex. 9 | Ex. 10 | Comp. Ex. 1 | Comp. Ex. 2 |
|---|---|---|---|---|---|---|---|---|---|---|---|---|
| Amount of LPO added (phm) | 1.8 | 1.8 | 1.8 | 1.8 | 1.8 | 1.8 | 1.8 | 1.8 | 1.8 | 1.8 | 1.8 | 1.8 |
| Polymerization temperature (° C.) | 42 | 42 | 42 | 42 | 42 | 42 | 42 | 42 | 42 | 42 | 42 | 42 |
| ELOCOL C0810 (phm) | 2 | 1 | 0 | 0 | 0 | 0 | 0 | 0 | 0 | 0 | 0 | 0 |
| ELOCOL C1214 (phm) | 0 | 0 | 2 | 1 | 0 | 0 | 0 | 0 | 0 | 0 | 0 | 0 |
| ELOCOL C1218 (phm) | 0 | 0 | 0 | 0 | 2 | 1 | 0 | 0 | 0 | 0 | 0 | 0 |
| ELOCOL C1899 (g) | 0 | 0 | 0 | 0 | 0 | 0 | 1320 | 660 | 0 | 0 | 0 | 0 |
| Chloride paraffin (g) | 0 | 0 | 0 | 0 | 0 | 0 | 0 | 0 | 1320 | 660 | 0 | 0 |
| Homogenization time (hr) | 2 | 2 | 2 | 2 | 2 | 2 | 2 | 2 | 2 | 2 | 2 | 3 |
| Polymerization time (min) | 652 | 595 | 568 | 597 | 612 | 526 | 579 | 576 | 592 | 574 | 558 | 541 |
| Average particle diameter (μm) | 0.52 | 0.62 | 0.59 | 0.63 | 0.61 | 0.62 | 0.69 | 0.70 | 0.74 | 0.71 | 0.68 | 0.62 |

TABLE 3

| Polymerization treatment | Ex. 11 | Ex. 12 | Ex. 13 | Ex. 14 | Ex. 15 | Ex. 16 | Comp. Ex. 3 | Comp. Ex. 4 |
|---|---|---|---|---|---|---|---|---|
| First seed (4.6 phm) | Ex. 2 | Ex. 4 | Ex. 5 | Ex. 6 | Ex. 8 | Ex. 10 | Comp. Ex. 1 | Comp. Ex. 2 |
| Polymerization temperature (° C.) | 55 | 55 | 55 | 55 | 55 | 55 | 55 | 55 |
| Polymerization time (min) | 260 | 300 | 294 | 275 | 326 | 340 | 375 | 336 |
| Scale (g) | 820 | 800 | 940 | 780 | 900 | 240 | 1630 | 1380 |

As can be seen from Table 2 above, comparing Examples 1 to 10 with Comparative Examples 1 to 2, Example shows a decrease in particle diameter. Furthermore, as can be seen from Table 3 above, comparing Examples 11 to 16 with Comparative Examples 3 to 4, Examples 11 to 16 shows reduced polymerization time.

[Amount of Remaining Monomer According to Addition of Monomer Absorption Accelerator]

The amounts of components added during respective polymerization were changed. In Comparative Example, aliphatic alcohol was not added. After completion of polymerization, amounts of remaining monomers during monomer recovery were identified.

Example 17

110 phm of deionized water, 1.7 phm of lauryl peroxide, 0.003 phm of paraquinone and 0.5 phm of higher aliphatic alcohol (C0810) as a monomer absorption accelerator were added to a 200 L high-pressure reactor, −730 mmHg of vacuum was applied to the 200 L high-pressure reactor, 100 phm of a vinyl chloride monomer and 1.6 phm of sodium dodecyl benzene sulfonate were added thereto, followed by agitating at a pressure of 3 kg/cm² for 20 minutes. Then, the resulting mixture was homogenized 65 cycles using the rotor stator-type homogenizer. After completion of homogenization, the reactor temperature was adjusted to 42° C. and polymerization was performed. Seed emulsion polymerization was performed at 61° C. using the seed thus obtained.

Example 18

A vinyl chloride polymer was prepared in the same manner as in Example 17, except that the amount of higher aliphatic alcohol added was 1 phm and the number of cycles was 50.

Example 19

A vinyl chloride polymer was prepared in the same manner as in Example 17, except that the amount of higher aliphatic alcohol added was 2 phm and the number of cycles was 40.

Comparative Example 5

A vinyl chloride polymer was prepared in the same manner as in Example 17, except that the higher aliphatic alcohol was not added and the number of cycles was 55.

Test Example

Amounts of remaining monomers of vinyl chloride polymers prepared in Examples 17 to 19 and Comparative Example 5 were measured through a flowmeter mounted on a recovery line.

Remaining monomer: amounts of remaining monomers were measured through a flowmeter mounted on a recovery line after polymerization.

Cumulative amount of removed heat: cumulative graph showing amounts of heat removed per minute during polymerization was plotted as a function of time until completion of reaction.

TABLE 4

|  |  | Ex. 17 | Ex. 18 | Ex. 19 | Comp. Ex. 5 |
|---|---|---|---|---|---|
| Seed | Aliphatic alcohol (phm) | 0.5 | 1 | 2 | Not added |
|  | The number of cycles | 65 | 50 | 40 | 55 |
| Main polymerization | Remaining monomer (kg) | 2.9 | 3 | 3.2 | 5.2 |

As can be seen from Table 4 above, Examples 17 to 19 considerably reduce amounts of remaining monomers which may affect physical properties of final latex after completion of polymerization and increase monomer consumption efficiency during polymerization when the vinyl chloride resin is polymerized using higher aliphatic alcohol. In addition, through comparison of graphs showing total cumulative amounts of removed heat in a case of using the monomer absorption accelerator and a case of not using the same, improvement in monomer consumption efficiency is confirmed and remaining monomers are relatively compared.

[Homogenization Using Rotor-Stator]

Example 20

105 phm of deionized water, 1.7 phm of lauryl peroxide, 0.003 phm of paraquinone and 1 phm of higher aliphatic alcohol as a monomer absorption accelerator were added to a 200 L high-pressure reactor, −730 mmHg of vacuum was applied to the 200 L high-pressure reactor, 100 phm of a vinyl chloride monomer and 1.6 phm of sodium dodecyl benzene sulfonate were added thereto, followed by agitating at a pressure of 3 kg/cm² for 20 minutes.

Then, the resulting mixture was homogenized 40 cycles at a rotor-stator gap of 0.5 mm using the rotor stator-type homogenizer. After completion of homogenization, the reactor temperature was adjusted to 40° C. and polymerization was performed.

Example 21

A vinyl chloride latex and a powdery paste vinyl chloride resin were prepared in the same manner as in Example 20, except that the number of cycles of the rotor stator was 80.

Example 22

A vinyl chloride latex and a powdery paste vinyl chloride resin were prepared in the same manner as in Example 20, except that the number of cycles of the rotor stator was 20.

Example 23

A vinyl chloride latex and a powdery paste vinyl chloride resin were prepared in the same manner as in Example 20, except that the rotor-stator gap was 0.3 mm.

Comparative Example 6

A vinyl chloride latex and a powdery paste vinyl chloride resin were prepared in the same manner as in Example 20, except that the swelling acceleration process was not performed.

Comparative Example 7

A vinyl chloride latex and a powdery paste vinyl chloride resin were prepared in the same manner as in Example 20, except that the swelling acceleration process was not performed and the amount of emulsifier added was 0.4 phm.

Comparative Example 8

A vinyl chloride latex and a powdery paste vinyl chloride resin were prepared in the same manner as in Example 20, except that the swelling acceleration process was not performed and the rotor-stator gap was adjusted to 1.5 mm.

Test Example

The average particle diameters and scale amounts of vinyl chloride polymers prepared in Examples 20 to 23 and Comparative Examples 6 to 8 were measured.
- Average particle diameter: particle diameter of prepared vinyl chloride latex was measured using Nanotrac 150 produced by Microtrac Inc.
- Scale amount: weight of substance trapped on strainer was roughly measured.

compared to Comparative Examples 6 to 8 in which swelling acceleration process is not performed.

[Effect According to Chain Length of Monomer Absorption Accelerator]

Monomer absorption accelerators having different chain lengths were added to respectively polymerize vinyl chloride resin seeds. Uniform-sized particles were prepared by controlling the number of cycles of the homogenizer (small-size particles were not prepared from long-chain C1899 and chloride paraffin) to prevent reduction of reaction time caused by decreased particle size. The seed thus polymerized was subjected to seed emulsion polymerization and the reduction of polymerization time according to chain length was compared.

Example 24

110 phm of deionized water, 1.7 phm of lauryl peroxide, 0.003 phm of paraquinone and 1 phm of higher aliphatic alcohol as a monomer absorption accelerator were added to a 200 L high-pressure reactor, −730 mmHg of vacuum was applied to the 200 L high-pressure reactor, and 100 phm of a vinyl chloride monomer and 1.6 phm of sodium dodecyl benzene sulfonate were added thereto, followed by agitating at a pressure of 3 kg/cm$^2$ for 20 minutes. Then, the resulting mixture was homogenized 45 cycles at a rotor stator gap of 0.5 mm using the rotor stator-type homogenizer. After completion of homogenization, the reactor temperature was adjusted to 42° C. and polymerization was performed. 4.6 phm of the seed thus polymerized was added to a 500 L reactor, the temperature was elevated to 55° C. and seed emulsion polymerization was performed.

Example 25

A vinyl chloride polymer was prepared in the same manner as in Example 24, except that the higher aliphatic alcohol was C1214 and the number of cycles of the rotor stator was 50.

Example 26

A vinyl chloride polymer was prepared in the same manner as in Example 24, except that the higher aliphatic alcohol was C1218 and the number of cycles of the rotor stator was 55.

TABLE 5

|  | Ex. 20 | Ex. 21 | Ex. 22 | Ex. 23 | Comp. Ex. 6 | Comp. Ex. 7 | Comp. Ex. 8 |
| --- | --- | --- | --- | --- | --- | --- | --- |
| The number of cycles | 40 | 80 | 20 | 40 | 40 | 40 | 40 |
| Swelling acceleration process | Performed | Performed | Performed | Performed | Not performed | Not performed | Not performed |
| Rotor-stator gap (mm) | 0.5 | 0.5 | 0.5 | 0.3 | 0.5 | 0.5 | 1.5 |
| Amount of emulsifier (phm) | 0.8 | 0.8 | 0.8 | 0.8 | 0.8 | 0.4 | 0.8 |
| Particle diameter (μm) | 0.65 | 0.42 | 0.91 | 0.58 | 0.68 | — | — |
| Scale | <100 g | <100 g | <100 g | <100 g | 780 g | Aggregated | Aggregated |

As can be seen from Table 5 above, Examples 20 to 23 exhibit superior droplet stability due to generation of less scale and provide particles having a size which could not be obtained by a conventional emulsifier control method, as

Example 27

A vinyl chloride polymer was prepared in the same manner as in Example 24, except that the higher aliphatic alcohol was C1299 and the number of cycles of the rotor stator was 70.

Example 28

A vinyl chloride polymer was prepared in the same manner as in Example 24, except that the higher aliphatic alcohol was chloride paraffin (Plastoil 152) and the number of cycles of the rotor stator was 70.

Comparative Example 9

A vinyl chloride polymer was prepared in the same manner as in Example 24, except that the higher aliphatic alcohol was not added and the number of cycles of the rotor stator was 60.

Test Example

Particles sizes of vinyl chloride polymers prepared in Examples 24 to 28 and Comparative Example 9 were measured using the following method and polymerization time was measured.

Average particle diameter: particle diameter of prepared vinyl chloride latex was measured using Nanotrac 150 produced by Microtrac Inc.

Polymerization time: time until the pressure of the reactor reached 3.5 kg/cm² after the completion of heating was measured.

TABLE 6

| | | Ex. 24 | Ex. 25 | Ex. 26 | Ex. 27 | Ex. 28 | Comp. Ex. 9 |
|---|---|---|---|---|---|---|---|
| Seed polymerization | Monomer absorption accelerator | C0810 | C1214 | C1218 | C1899 | Chloride paraffin | — |
| | Amount of added (phm) | 1 | 1 | 1 | 1 | 1 | — |
| | Size (μm) | 0.63 | 0.63 | 0.62 | 0.70 | 0.72 | 0.62 |
| Main polymerization temperature (° C.) | | 55 | 55 | 55 | 55 | 55 | 55 |
| Amount of seed added (phm) | | 4.6 | 4.6 | 4.6 | 4.6 | 4.6 | 4.6 |
| Reaction time (hour:min) | | 4:20 | 5:00 | 4:45 | 5:26 | 5:40 | 5:46 |

As can be seen from Table 6 above, Examples 24 to 28 in which vinyl chloride resins are polymerized using higher aliphatic alcohol show reduced reaction time and thus improved polymerization production efficiency. In addition, as chain length of higher aliphatic alcohol decreases, reaction time is more effectively reduced.

[Control of Particle Diameter of Vinyl Chloride Resin According to Addition of Monomer Absorption Accelerator]

Example 29

110 phm of deionized water, 1.7 phm of lauryl peroxide, 0.003 phm of paraquinone and 2 phm of a higher aliphatic alcohol mixture ($C_8:C_{10}$=55:45, weight ratio) as a monomer absorption accelerator were added to a 200 L high-pressure reactor, −730 mmHg of vacuum was applied to the 200 L high-pressure reactor, 100 phm of a vinyl chloride monomer and 1.6 phm of sodium dodecyl benzene sulfonate were added thereto, followed by agitating at a pressure of 3 kg/cm² for 20 minutes. Then, the resulting mixture was homogenized 45 cycles using the rotor stator-type homogenizer. After completion of homogenization, the reactor temperature was adjusted to 42° C. and polymerization was performed.

Example 30

Polymerization was performed in the same manner as in Example 29, except that the amount of higher aliphatic alcohol added was 1 phm.

Example 31

Polymerization was performed in the same manner as in Example 29, except that the higher aliphatic alcohol added was a higher aliphatic alcohol mixture of $C_{12}:C_{14}$=55:45 (weight ratio).

Example 32

Polymerization was performed in the same manner as in Example 29, except that the amount of higher aliphatic alcohol added was 2 phm.

Example 33

Polymerization was performed in the same manner as in Example 29, except that the higher aliphatic alcohol added was C1218 (C1214 65 wt %, C1618 35 wt %).

Example 34

Polymerization was performed in the same manner as in Example 33, except that the amount of higher aliphatic alcohol added was 1 phm.

Example 35

Polymerization was performed in the same manner as in Example 29, except that the higher aliphatic alcohol was 99% by weight of C18.

Example 36

Polymerization was performed in the same manner as in Example 35, except that the amount of higher aliphatic alcohol added was 2 phm.

Comparative Example 10

Polymerization was performed in the same manner as in Example 29, except that the higher aliphatic alcohol was not added.

Test Example

Particles sizes of vinyl chloride polymers prepared in Examples and Comparative Examples were measured using the following method.

Average particle diameter: particle diameter (MV) of prepared vinyl chloride latex was measured using Nanotrac 150 produced by Microtrac Inc.

Stability of particles: amount of scale trapped on strainer when blowing down polymerized latex was measured.

TABLE 7

| Item | Ex. 29 | Ex. 30 | Ex. 31 | Ex. 32 | Ex. 33 | Ex. 34 | Ex. 35 | Ex. 36 | Comp. Ex. 10 |
|---|---|---|---|---|---|---|---|---|---|
| C810 | 2 | 1 | 0 | 0 | 0 | 0 | 0 | 0 | 0 |
| C1214 | 0 | 0 | 2 | 1 | 0 | 0 | 0 | 0 | 0 |
| C1218 | 0 | 0 | 0 | 0 | 2 | 1 | 0 | 0 | 0 |
| C1899 | 0 | 0 | 0 | 0 | 0 | 0 | 2 | 1 | 0 |
| The number of cycles | 45 | 45 | 45 | 45 | 45 | 45 | 45 | 45 | 45 |
| MV (μm) | 0.527 | 0.599 | 0.594 | 0.638 | 0.615 | 0.650 | 0.691 | 0.704 | 0.688 |
| Scale | ≤100 g | ≤100 g | ≤100 g | ≤100 g | ≤100 g | ≤100 g | ≤100 g | ≤100 g | 240 g |

As can be seen from Table 7 above, in Examples 29 to 36 in which higher aliphatic alcohol is added before addition of the vinyl chloride monomer, particle diameters (MV) of final paste vinyl chloride resins are controlled according to the type and amount of higher aliphatic alcohol added.

For reference, Comparative Example 10 in which higher aliphatic alcohol is not added shows a particle diameter of 0.688 μm, but the particle diameter (MV) of the final paste vinyl chloride resin is adjusted to 0.527 μm under the same homogenization conditions due to the addition of higher aliphatic alcohol.

In addition, the final paste vinyl chloride resin particles prepared according to the present invention have improved stability as compared to particles prepared in Comparative Example 10.

INDUSTRIAL APPLICABILITY

In accordance with the method according to the present invention employing a certain seed prepared using the monomer absorption accelerator of the present invention as a first seed for seed emulsion polymerization, polymerization reactivity is excellent and polymerization time is thus reduced, as compared to a conventional method. In addition, the method minimizes an amount of remaining monomer which affects physical properties of final latex after completion of polymerization of vinyl chloride resin and provides latex having superior polymerization stability, increases monomer consumption during polymerization, reduces reaction time, improves production efficiency and reduces amount of scale.

Particle size can be controlled by an easy and simple method through addition of a monomer absorption accelerator and control range thereof thus widens without separately controlling devices required for controlling particle size, the number of cycles and pressure.

What is claimed is:

1. A monomer absorption accelerator for preparing vinyl chloride resins, comprising:
   at least two higher aliphatic alcohols represented by Formula 1:

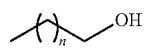

[Formula 1]

wherein n is an integer of 6 to 16.

2. The monomer absorption accelerator according to claim 1, wherein the at least two higher aliphatic alcohols are selected from the group consisting of $C_8$ higher aliphatic alcohol, $C_{10}$ higher aliphatic alcohol, $C_{12}$ higher aliphatic alcohol, $C_{14}$ higher aliphatic alcohol, $C_{16}$ higher aliphatic alcohol and $C_{18}$ higher aliphatic alcohol.

3. The monomer absorption accelerator according to claim 1, wherein the higher aliphatic alcohol has a solubility in water, of 10,000 to 0.001 mg/L.

4. A monomer absorption accelerator-based composition for vinyl chloride resins, comprising:
   a vinyl chloride monomer;
   an emulsifier;
   an initiator;
   a polymerization inhibitor; and
   the at least two the higher aliphatic alcohols according to claim 1.

5. The monomer absorption accelerator-based composition for vinyl chloride resins according to claim 4, wherein the at least two higher aliphatic alcohols serve as both a monomer absorption accelerator and an auxiliary emulsifier.

6. The monomer absorption accelerator-based composition for vinyl chloride resins according to claim 4, wherein each of the at least two higher aliphatic alcohols is $C_8$ to $C_{18}$ higher aliphatic alcohol.

7. The monomer absorption accelerator-based composition for vinyl chloride resins according to claim 6, wherein the at least two higher aliphatic are selected from the group consisting of $C_8$ higher aliphatic alcohol, $C_{10}$ higher aliphatic alcohol, $C_{12}$ higher aliphatic alcohol, $C_{14}$ higher aliphatic alcohol, $C_{16}$ higher aliphatic alcohol and $C_{18}$ higher aliphatic alcohol.

8. The monomer absorption accelerator-based composition for vinyl chloride resins according to claim 4, wherein the at least two higher aliphatic alcohols are present in an amount of 0.1 phm to 10 phm with respect to the vinyl chloride monomer.

9. A method for preparing a vinyl chloride seed comprising:
   adding a vinyl chloride monomer, an emulsifier and a polymerization initiator to an aqueous medium;
   homogenizing droplets using a homogenizer pump; and
   polymerizing the homogenized droplets,
   wherein the monomer absorption accelerator of claim 1 is added before the polymerization, and the polymerization is performed after the homogenization.

10. The method according to claim 9, wherein each of the higher aliphatic alcohols has a solubility in water, of 10,000 to 0.001 mg/L.

11. The method according to claim 9, wherein each of the higher aliphatic alcohols is $C_8$ to $C_{18}$ higher aliphatic alcohol.

12. The method according to claim 9, wherein the at least two higher aliphatic alcohols are selected from the group consisting of $C_8$ higher aliphatic alcohol, $C_{10}$ higher aliphatic alcohol, $C_{12}$ higher aliphatic alcohol, $C_{14}$ higher aliphatic alcohol, $C_{16}$ higher aliphatic alcohol and $C_{18}$ higher aliphatic alcohol.

13. The method according to claim 9, wherein the monomer absorption accelerator is used in an amount of 0.1 to 10 phm for preparation of vinyl chloride polymers.

14. The method according to claim 9, wherein the polymerization is performed at a temperature of 40 to 50° C. for 9 to 12 hours.

15. A method for preparing a vinyl chloride seed comprising:
  swelling acceleration including adding polymerization water, a vinyl chloride monomer, an emulsifier and the monomer absorption accelerator of claim 1 to a pre-mixing tank, followed by agitating to obtain a mixture;
  passing the mixture through a rotary homogenizer to homogenize the mixture; and
  polymerizing the homogenized mixture in a reactor.

16. The method according to claim 15, wherein the polymerization water is added in an amount of 20 to 150 parts by weight, the emulsifier is added in an amount of 0.1 to 10 parts by weight and the monomer absorption accelerator is added in an amount of 0.1 to 10 parts by weight, based on 100 parts by weight of the vinyl chloride monomer.

17. The method according to claim 15, wherein the emulsifier comprises at least one selected from the group consisting of sodium lauryl sulfate (SLS), sodium dodecyl benzene sulfonate (SDBS), sodium dodecyl alkylsulfate (SDS), ammonium lauryl sulfate (ALS), sodium cetyl stearyl sulfate, sodium lauryl ether sulfate (SLES) and succinate.

18. The method according to claim 15, wherein the swelling acceleration comprises agitating the components at a pressure of 0.1 to 5 $kg/cm^2$ for 5 to 60 minutes.

19. The method according to claim 15, wherein the homogenization is carried out using a homogenization pump for 1 to 3 hours and the number of cycles of the rotary homogenizer is 10 to 150 and a rotor-stator gap is 0.05 to 10 mm.

20. A method for polymerizing a latex comprising:
  adding reaction water and the monomer absorption accelerator-based composition of claim 4 to a reactor for latex polymerization, followed by homogenization and polymerization.

21. The method according to claim 20, wherein a type and amount of the monomer absorption accelerator are controlled according to particle diameter of final paste vinyl chloride resin to be obtained.

22. A paste vinyl chloride resin obtained by the latex polymerization method according to claim 20, wherein the particle diameter (MV) of the final paste vinyl chloride resin is varied under the same homogenization conditions according to the type and amount of the higher aliphatic alcohol used.

23. A vinyl chloride seed prepared by the method according to claim 9.

24. A paste vinyl chloride resin prepared by performing seed emulsion polymerization using 3 to 15 phm of the vinyl chloride seed according to claim 9 as a first seed at 50 to 65° C. for 4 to 6 hours.

\* \* \* \* \*